US009326551B2

(12) United States Patent
Hon

(10) Patent No.: US 9,326,551 B2
(45) Date of Patent: *May 3, 2016

(54) ELECTRONIC CIGARETTE

(71) Applicant: FONTEM HOLDINGS 1 B.V., Amsterdam (NL)

(72) Inventor: Lik Hon, North Point (HK)

(73) Assignee: Fontem Holdings 1 B.V., Amsterdam (NL)

(*) Notice: Subject to any disclaimer, the term of this patent is extended or adjusted under 35 U.S.C. 154(b) by 0 days.

This patent is subject to a terminal disclaimer.

(21) Appl. No.: 14/723,209

(22) Filed: May 27, 2015

(65) Prior Publication Data

US 2015/0250231 A1 Sep. 10, 2015

Related U.S. Application Data

(63) Continuation of application No. 13/754,521, filed on Jan. 30, 2013, which is a continuation of application No. 12/226,819, filed as application No. PCT/CN2007/001576 on May 15, 2007, now Pat. No. 8,375,957.

(30) Foreign Application Priority Data

May 16, 2006 (CN) .................. 2006 2 0090805 U

(51) Int. Cl.
*A24F 13/00* (2006.01)
*A24F 17/00* (2006.01)
(Continued)

(52) U.S. Cl.
CPC ............. *A24F 47/008* (2013.01); *A24F 47/002* (2013.01); *A24F 47/004* (2013.01); *F22B 1/284* (2013.01); *H01M 2/1055* (2013.01);
(Continued)

(58) Field of Classification Search
None
See application file for complete search history.

(56) References Cited

U.S. PATENT DOCUMENTS 705,919 A 7/1902 Gill
2,057,353 A 10/1936 Whittemore
(Continued)

FOREIGN PATENT DOCUMENTS

CA 2752134 11/2004
CA 2562581 A1 10/2005
(Continued)

OTHER PUBLICATIONS

U.S. District Court, Central District of California, Western Division, Defendant NJOY, Inc.'s Memorandum of Points and Authorities in Support of Defendants' Motion for Leave to Amend Invalidity Contentions dated Jun. 29, 2015 and filed in Consolidated Case No. CV 14-01645 GW (MRW) and related consolidated cases.
(Continued)

*Primary Examiner* — Michael H Wilson
*Assistant Examiner* — Phu Nguyen
(74) *Attorney, Agent, or Firm* — Perkins Coie LLP

(57) ABSTRACT

An electronic cigarette includes a battery assembly, an atomizer assembly and a cigarette bottle assembly. An external thread electrode is located in one end of battery assembly. An internal thread electrode is located in one end of atomizer assembly. The battery assembly and the atomizer assembly are connected by the screwthread electrode. The cigarette bottle assembly is inserted into the other end of the atomizer assembly and both form a cigarette type or cigar type body.

15 Claims, 10 Drawing Sheets

(51) Int. Cl.

| | |
|---|---|
| A24F 25/00 | (2006.01) |
| A24F 47/00 | (2006.01) |
| H05B 1/02 | (2006.01) |
| H05B 3/06 | (2006.01) |
| H05B 3/42 | (2006.01) |
| F22B 1/28 | (2006.01) |
| H01M 2/10 | (2006.01) |
| H01M 10/42 | (2006.01) |
| H01M 10/46 | (2006.01) |
| H02J 7/00 | (2006.01) |

(52) U.S. Cl.
CPC ............ *H01M10/425* (2013.01); *H01M 10/46* (2013.01); *H02J 7/0042* (2013.01); *H02J 7/0052* (2013.01); *H05B 1/0244* (2013.01); *H05B 1/0297* (2013.01); *H05B 3/06* (2013.01); *H05B 3/42* (2013.01)

(56) References Cited

U.S. PATENT DOCUMENTS

| | | | |
|---|---|---|---|
| 3,200,819 | A | 8/1965 | Gilbert |
| 4,945,929 | A | 8/1990 | Egilmex |
| 5,894,841 | A | 4/1999 | Voges |
| 6,196,218 | B1 | 3/2001 | Voges |
| 6,601,776 | B1 | 8/2003 | Oljaca |
| 6,715,494 | B1 | 4/2004 | McCoy |
| 8,156,944 | B2 | 4/2012 | Hon |
| 2005/0016550 | A1 | 1/2005 | Katase |
| 2006/0196518 | A1 | 9/2006 | Hon |
| 2007/0267031 | A1 | 11/2007 | Hon |
| 2008/0257367 | A1 | 10/2008 | Paterno |

FOREIGN PATENT DOCUMENTS

| | | |
|---|---|---|
| CA | 2647212 | 5/2006 |
| CN | 1135860 A | 11/1996 |
| CN | 1196660 A | 11/1996 |
| CN | 1191696 A | 9/1998 |
| CN | 1252961 A | 5/2000 |
| CN | 1106812 C | 4/2003 |
| CN | 1530041 A | 9/2004 |
| CN | 1541577 A | 11/2004 |
| CN | 1575673 A | 2/2005 |
| CN | 2719043 Y | 8/2005 |
| CN | 2777995 Y | 5/2006 |
| CN | 201797997 U | 4/2011 |
| CN | 202026802 U | 11/2011 |
| CN | 202026804 U | 11/2011 |
| EP | 0057243 A1 | 8/1982 |
| EP | 0845220 A1 | 6/1998 |
| EP | 01618803 A1 | 1/2006 |
| EP | 01618808 A1 | 1/2006 |
| EP | 01736065 A1 | 12/2006 |
| WO | WO9421317 | 9/1994 |
| WO | WO2004080216 | 9/2004 |
| WO | WO2005099494 | 10/2005 |

OTHER PUBLICATIONS

U.S. District Court, Central District of California, Western Division, Defendant NJOY, Inc.'s Declaration of Brent K. Yamashita in Support of Defendants' Motion for Leave to Amend Invalidity Contentions dated Jun. 29, 2015 and filed in Consolidated Case No. Cv 14-01645 GW (MRW) and related consolidated cases.
U.S. District Court, Central District of California, Western Division, Defendant NJOY, Inc.'s Exhibit 1 to Defendants' Motion for Leave to Amend Invalidity Contentions dated Jun. 29, 2015 and filed in Consolidated case No. CV 14-01645 GW (MRW) and related consolidated cases.
U.S. District Court, Central District of California, Western Division, Defendant NJOY, Inc.'s Exhibit 2 to Defendants' Motion for Leave to Amend Invalidity Contentions dated Jun. 29, 2015 and filed in Consolidated case No. CV 14-01645 GW (MRW) and related consolidated cases.
U.S. District Court, Central District of California, Western Division, Defendant NJOY, Inc.'s Exhibit 3 to Defendants' Motion for Leave to Amend Invalidity Contentions dated Jun. 29, 2015 and filed in Consolidated case No. CV 14-01645 GW (MRW) and related consolidated cases.
U.S. District Court, Central District of California, Western Division, Defendant NJOY, Inc.'s Exhibit 4 to Defendants' Motion for Leave to Amend Invalidity Contentions dated Jun. 29, 2015 and filed in Consolidated case No. CV 14-01645 GW (MRW) and related consolidated cases.
U.S. District Court, Central District of California, Western Division, Defendant NJOY, Inc.'s Exhibit 5 to Defendants' Motion for Leave to Amend Invalidity Contentions dated Jun. 29, 2015 and filed in Consolidated case No. CV 14-01645 GW (MRW) and related consolidated cases.
U.S. District Court, Central District of California, Western Division, Defendant NJOY, Inc.'s Reply Brief in Support of Defendants' Motion for Leave to Amend Invalidity Contentions dated Jul. 13, 2015 and filed in consolidated Case No. CV 14-01645 GW (MRW) and related consolidated cases.
U.S. District Court, Central District of California, Western Division, Defendant NJOY, Inc.'s production documents VLACHOS 0000061-72; Consolidated Case No. CV 14-01645 GW (MRW) and related consolidated cases.
Chen, Yongzhi—Patent Invalidation Petition against CN200620090805.0, Case No. 5W1014616 with English Translation, May 31, 2013.
Chen, Yongzhi—Patent Invalidation Petition against CN200620090805.0, Case No. 5W1014616, May 31, 2013, D1-CN2719043.
Chen, Yongzhi—Patent Invalidation Petition against CN200620090805.0, Case No. 5W1014616, May 31, 2013, D2-CN1196660.
Collins, John M., Expert Report—Invalidity, CV14-01645, Jun. 18, 2015.
Collins, John M., Expert Report—Invalidity, CV14-01645—Appendix J-1 Invalidity Claim Chart for U.S. Pat. No. 8,863,752, Jun. 18, 2015.
Collins, John M., Expert Report—Invalidity, CV14-01645—Appendix J-2 Invalidity Claim Chart for U.S. Pat. No. 8,863,752, Jun. 18, 2015.
Collins, John M., Expert Report—Invalidity, CV14-01645—Appendix J-3 Invalidity Claim Chart for U.S. Pat. No. 8,863,752, Jun. 18, 2015.
Collins, John M., Expert Report—Invalidity, CV14-01645—Appendix J-4 Invalidity Claim Chart for U.S. Pat. No. 8,863,752, Jun. 18, 2015.
Collins, John M., Expert Report—Invalidity, CV14-01645—Appendix J-5 Invalidity Claim Chart for U.S. Pat. No. 8,863,752, Jun. 18, 2015.
Collins, John M., Expert Report—Invalidity, CV14-01645—Appendix J-6 Invalidity Claim Chart for U.S. Pat. No. 8,863,752, Jun. 18, 2015.
Collins, John M., Expert Report—Invalidity, CV14-01645—Appendix F-1 Invalidity Claim Chart for U.S. Pat. No. 8,375,957, Jun. 18, 2015.
Collins, John M., Expert Report—Invalidity, CV14-01645—Appendix F-2 Invalidity Claim Chart for U.S. Pat. No. 8,375,957, Jun. 18, 2015.
Collins, John M., Expert Report—Invalidity, CV14-01645—Appendix F-3 Invalidity Claim Chart for U.S. Pat. No. 8,375,957, Jun. 18, 2015.
Collins, John M., Expert Report—Invalidity, CV14-01645—Appendix F-4 Invalidity Claim Chart for U.S. Pat. No. 8,375,957, Jun. 18, 2015.
Collins, John M., Expert Report—Invalidity, CV14-01645, Jun. 18, 2015—Exhibit 21, U.S. Pat. No. 2,057,353 Whittemore.
Collins, John M., Expert Report—Invalidity, CV14-01645, Jun. 18, 2015—Exhibit 22, U.S. Pat. No. 5,894,841 Voges.

(56) References Cited

OTHER PUBLICATIONS

Collins, John M., Expert Report—Invalidity, CV14-01645, Jun. 18, 2015—Exhibit 25, EP0845220B1 Susa.
Collins, John M., Expert Report—Invalidity, CV14-01645, Jun. 18, 2015—Exhibit 26, U.S. Pat. No. 3,200,819 Gilbert.
Collins, John M., Expert Report—Invalidity, CV14-01645, Jun. 18, 2015—Exhibit 63, U.S. Pat. No. 6,196,218 Voges '218.
Collins, John M., Expert Report—Invalidity, CV14-01645, Jun. 18, 2015—Exhibit 75, CA2752134 Hon '134.
Collins, John M., Expert Report—Invalidity, CV14-01645, Jun. 18, 2015—Exhibit 76, WO2005099494 Hon '494.
Collins, John M., Expert Report—Invalidity, CV14-01645, Jun. 18, 2015—Exhibit 77, CN2719043 Hon '043.
Collins, John M., Expert Report—Invalidity, CV14-01645, Jun. 18, 2015—Exhibit 78, TECHPOWERUP, www.techpowerup.com— "What is a MOSFET, what does it look like, and how does it work?"—published May 24, 2004.
Collins, John M., Expert Report—Invalidity, CV14-01645, Jun. 18, 2015—Exhibit 79, US20070267031 Hon '031.
Collins, John M., Expert Report—Invalidity, CV14-01645, Jun. 18, 2015—Exhibit 82, U.S. Pat. No. 0,705,919 Gill.
Collins, John M., Expert Report—Invalidity, CV14-01645, Jun. 18, 2015—Exhibit 84, EP0845220A1 Susa.
Collins, John M., Expert Report—Invalidity, CV14-01645, Jun. 18, 2015—Exhibit 103, certified English translation of CN2719043 Hon '043 Translation.
Collins, John M., Expert Report—Invalidity, CV14-01645, Jun. 18, 2015—Exhibit 104, certified English translation of WO2005099494 Hon '494 Translation.
ITC Limited, Representation for Opposition to Grant of Patent against IN8529/DELNP/2008, May 11, 2015.
ITC Limited, Representation for Opposition to Grant of Patent against IN8529/DELNP/2008, May 11, 2015, D1-CN2719043.
ITC Limited, Representation for Opposition to Grant of Patent against IN8529/DELNP/2008, May 11, 2015, D1 Equivalent—EP1736065.
ITC Limited, Representation for Opposition to Grant of Patent against IN8529/DELNP/2008, May 11, 2015, D2—WO1994021317.
ITC Limited, Representation for Opposition to Grant of Patent against IN8529/DELNP/2008, May 11, 2015, D3—U.S. Pat. No. 6,601,776.
ITC Limited, Representation for Opposition to Grant of Patent against IN8529/DELNP/2008, May 11, 2015, D4—EP01618803A.
IP Australia, Patent Examination Report No. 1 for AU2007250368, Aug. 9, 2012.
IP Office India, First Examination Report for 8529/DELNP/2008, Jun. 25, 2015.
IP Office New Zealand, Exam Report for NZ572310, Apr. 29, 2010.
JT International S.A., Petition for Inter Partes Review of U.S. Pat. No. 8,375,957—IPR2015-01513, Paper 1, Jun. 26, 2015.
JT International S.A., Petition for Inter Partes Review of U.S. Pat. No. 8,375,957—IPR2015-01513, Exhibit 1001, U.S. Pat. No. 8,375,957 to Hon , Jun. 26, 2015.
JT International S.A., Petition for Inter Partes Review of U.S. Pat. No. 8,375,957—IPR2015-01513, Exhibit 1002, Schuster Expert Declaration , Jun. 26, 2015.
JT International S.A., Petition for Inter Partes Review of U.S. Pat. No. 8,375,957—IPR2015-01513, Exhibit 1003, Canadian Patent Application No. 2 752 134 to Hon , Jun. 26, 2015.
JT International S.A., Petition for Inter Partes Review of U.S. Pat. No. 8,375,957—IPR2015-01513, Exhibit 1004, U.S. Pat. No. 6,234,167 to Cox , Jun. 26, 2015.
JT International S.A., Petition for Inter Partes Review of U.S. Pat. No. 8,375,957—IPR2015-01513, Exhibit 1005, EP 0 845 220 A1 to Susa , Jun. 26, 2015.
JT International S.A., Petition for Inter Partes Review of U.S. Pat. No. 8,375,957—IPR2015-01513, Exhibit 1006, U.S. Pat. No. 5,060,671 to Counts , Jun. 26, 2015.
JT International S.A., Petition for Inter Partes Review of U.S. Pat. No. 8,375,957—IPR2015-01513, Exhibit 1007, U.S. Pat. No. 6,155,268 to Takeuchi , Jun. 26, 2015.
JT International S.A., Petition for Inter Partes Review of U.S. Pat. No. 8,375,957—IPR2015-01513, Exhibit 1008, WO 00/28843 A1 to Pienemann , Jun. 26, 2015.
JT International S.A., Petition for Inter Partes Review of U.S. Pat. No. 8,375,957—IPR2015-01513, Exhibit 1009, Certified English translation of WO 00/28843 A1 to Pienemann , Jun. 26, 2015.
JT International S.A., Petition for Inter Partes Review of U.S. Pat. No. 8,375,957—IPR2015-01513, Exhibit 1010, CN 2719043 to Hon , Jun. 26, 2015.
JT International S.A., Petition for Inter Partes Review of U.S. Pat. No. 8,375,957—IPR2015-01513, Exhibit 1011, Certified English translation of CN 2719043 to Hon , Jun. 26, 2015.
JT International S.A., Petition for Inter Partes Review of U.S. Pat. No. 8,375,957—IPR2015-01513, Exhibit 1012, U.S. Pat. No. 2,057,353 to Whittemore , Jun. 26, 2015.
JT International S.A., Petition for Inter Partes Review of U.S. Pat. No. 8,375,957—IPR2015-01513, Exhibit 1013, U.S. Patent Publication No. 2003/0033055 A1 to McRae , Jun. 26, 2015.
JT International S.A., Petition for Inter Partes Review of U.S. Pat. No. 8,375,957—IPR2015-01513, Exhibit 1014, CN200620090805 to Hon , Jun. 26, 2015.
JT International S.A., Petition for Inter Partes Review of U.S. Pat. No. 8,375,957—IPR2015-01513, Exhibit 1015, Certified English translation of CN200620090805 to Hon , Jun. 26, 2015.
JT International S.A., Petition for Inter Partes Review of U.S. Pat. No. 8,375,957—IPR2015-01513, Exhibit 1016, Oct. 5, 2010 Office Action ('957) , Jun. 26, 2015.
JT International S.A., Petition for Inter Partes Review of U.S. Pat. No. 8,375,957—IPR2015-01513, Exhibit 1017, Mar. 7, 2011 Response ('957) , Jun. 26, 2015.
JT International S.A., Petition for Inter Partes Review of U.S. Pat. No. 8,375,957—IPR2015-01513, Exhibit 1018, Jun. 8, 2011 Office Action ('957) , Jun. 26, 2015.
JT International S.A., Petition for Inter Partes Review of U.S. Pat. No. 8,375,957—IPR2015-01513, Exhibit 1019, Dec. 8, 2011 Response ('957) , Jun. 26, 2015.
JT International S.A., Petition for Inter Partes Review of U.S. Pat. No. 8,375,957—IPR2015-01513, Exhibit 1020, Jan. 9, 2012 Office Action ('957) , Jun. 26, 2015.
JT International S.A., Petition for Inter Partes Review of U.S. Pat. No. 8,375,957—IPR2015-01513, Exhibit 1021, May 9, 2012 Response ('957) , Jun. 26, 2015.
JT International S.A., Petition for Inter Partes Review of U.S. Pat. No. 8,375,957—IPR2015-01513, Exhibit 1022, Aug. 7, 2012 Office Action ('957) , Jun. 26, 2015.
JT International S.A., Petition for Inter Partes Review of U.S. Pat. No. 8,375,957—IPR2015-01513, Exhibit 1023, Aug. 29, 2012 Response ('957) , Jun. 26, 2015.
JT International S.A., Petition for Inter Partes Review of U.S. Pat. No. 8,375,957—IPR2015-01513, Exhibit 1024, Dec. 17, 2012 Notice of Allowance ('957) , Jun. 26, 2015.
JT International S.A., Petition for Inter Partes Review of U.S. Pat. No. 8,375,957—IPR2015-01513, Exhibit 1025, McGraw-Hill Dictionary of Scientific and Technical Terms (5th ed. 1994) , Jun. 26, 2015.
JT International S.A., Petition for Inter Partes Review of U.S. Pat. No. 8,375,957—IPR2015-01513, Exhibit 1026, Academic Press Dictionary of Science and Technology (1992) , Jun. 26, 2015.
JT International S.A., Petition for Inter Partes Review of U.S. Pat. No. 8,375,957—IPR2015-01513, Exhibit 1027, American Heritage Dictionary of the English Language (1996) , Jun. 26, 2015.
JT International S.A., Petition for Inter Partes Review of U.S. Pat. No. 8,375,957—IPR2015-01513, Exhibit 1028, KR 10-0469625 to Kim , Jun. 26, 2015.
JT International S.A., Petition for Inter Partes Review of U.S. Pat. No. 8,375,957—IPR2015-01513, Exhibit 1029, Certified English translation of KR 10-0469625 to Kim , Jun. 26, 2015.
JT International S.A., Petition for Inter Partes Review of U.S. Pat. No. 8,375,957—IPR2015-01513, Exhibit 1030, U.S. Pat. No. 1,446,087 to Griffin , Jun. 26, 2015.

(56) References Cited

OTHER PUBLICATIONS

JT International S.A., Petition for Inter Partes Review of U.S. Pat. No. 8,375,957—IPR2015-01513, Exhibit 1031, Curriculum Vitae of Jeffrey Arthur Schuster, Ph.D., Jun. 26, 2015.
JT International S.A., Petition for Inter Partes Review of U.S. Pat. No. 8,375,957—IPR2015-01513, Exhibit 1032, J.A. Speck, Mechanical Fastening, Joining and Assembly (1997), Jun. 26, 2015.
JT International S.A., Petition for Inter Partes Review of U.S. Pat. No. 8,375,957—IPR2015-01513, Exhibit 1033, U.S. Pat. No. 705,919 to Gill, Jun. 26, 2015.
JT International S.A., Petition for Inter Partes Review of U.S. Pat. No. 8,375,957—IPR2015-01513, Exhibit 1034, U.S. Pat. No. 980,830 to Patterson, Jun. 26, 2015.
JT International S.A., Petition for Inter Partes Review of U.S. Pat. No. 8,375,957—IPR2015-01513, Exhibit 1035, U.S. Pat. No. 6,070,992 to Schnell, Jun. 26, 2015.
JT International S.A., Petition for Inter Partes Review of U.S. Pat. No. 8,375,957—IPR2015-01513, Exhibit 1036, U.S. Pat. No. 3,934,117 to Schladitz, Jun. 26, 2015.
JT International S.A., Petition for Inter Partes Review of U.S. Pat. No. 8,375,957—IPR2015-01513, Exhibit 1037, U.S. Pat. No. 4,531,178 to Uke, Jun. 26, 2015.
JT International S.A., Petition for Inter Partes Review of U.S. Pat. No. 8,375,957—IPR2015-01513, Exhibit 1038, U.S. Pat. No. 5,177,424 to Connors, Jun. 26, 2015.
JT International S.A., Petition for Inter Partes Review of U.S. Pat. No. 8,375,957—IPR2015-01513, Exhibit 1039, U.S. Pat. No. 6,232,784 to Dulasky, Jun. 26, 2015.
JT International S.A., Petition for Inter Partes Review of U.S. Pat. No. 8,863,752—IPR2015-01604, Paper 1, Jul. 20, 2015.
JT International S.A., Petition for Inter Partes Review of U.S. Pat. No. 8,863,752—IPR2015-01604, Exhibit 1001, U.S. Pat. No. 8,863,752 to Hon, Jul. 20, 2015.
JT International S.A., Petition for Inter Partes Review of U.S. Pat. No. 8,863,752—IPR2015-01604, Exhibit 1002, Declaration of Jeffrey A. Schuster, Ph.D., Jul. 20, 2015.
JT International S.A., Petition for Inter Partes Review of U.S. Pat. No. 8,863,752—IPR2015-01604, Exhibit 1003, U.S. Pat. No. 8,375,957 Certificate of Correction, Jul. 20, 2015.
JT International S.A., Petition for Inter Partes Review of U.S. Pat. No. 8,863,752—IPR2015-01604, Exhibit 1004, '752 Patent Application as Filed, Jul. 20, 2015.
JT International S.A., Petition for Inter Partes Review of U.S. Pat. No. 8,863,752—IPR2015-01604, Exhibit 1005, Restriction Requirement, Jul. 20, 2015.
JT International S.A., Petition for Inter Partes Review of U.S. Pat. No. 8,863,752—IPR2015-01604, Exhibit 1006, Response to Restriction Requirement, Jul. 20, 2015.
JT International S.A., Petition for Inter Partes Review of U.S. Pat. No. 8,863,752—IPR2015-01604, Exhibit 1007, Non-Final Office Action, Jul. 20, 2015.
JT International S.A., Petition for Inter Partes Review of U.S. Pat. No. 8,863,752—IPR2015-01604, Exhibit 1008, Response to Non-Final Office Action, Jul. 20, 2015.
JT International S.A., Petition for Inter Partes Review of U.S. Pat. No. 8,863,752—IPR2015-01604, Exhibit 1009, Notice of Allowance, Jul. 20, 2015.
JT International S.A., Petition for Inter Partes Review of U.S. Pat. No. 8,863,752—IPR2015-01604, Exhibit 1010, McGraw-Hill Dictionary of Scientific and Technical Terms ("assembly") ("component") ("electrode") ("pore") ("porous") ("screwthread"), Jul. 20, 2015.
JT International S.A., Petition for Inter Partes Review of U.S. Pat. No. 8,863,752—IPR2015-01604, Exhibit 1011, American Heritage Dictionary ("atomize") ("flow"), Jul. 20, 2015.
JT International S.A., Petition for Inter Partes Review of U.S. Pat. No. 8,863,752—IPR2015-01604, Exhibit 1012, Merriam-Webster.com ("aerosol") ("atomizer") ("contain") ("housing") ("insert") ("paper") ("permeable") ("store"), Jul. 20, 2015.
JT International S.A., Petition for Inter Partes Review of U.S. Pat. No. 8,863,752—IPR2015-01604, Exhibit 1013, Academic Press Dictionary of Science and Technology ("permeability") ("solid"), Jul. 20, 2015.
JT International S.A., Petition for Inter Partes Review of U.S. Pat. No. 8,863,752—IPR2015-01604, Exhibit 1014, Canadian Patent Application No. 2 752 134 to Hon, Jul. 20, 2015.
JT International S.A., Petition for Inter Partes Review of U.S. Pat. No. 8,863,752—IPR2015-01604, Exhibit 1015, U.S. Pat. No. 6,155,268 to Takeuchi, Jul. 20, 2015.
JT International S.A., Petition for Inter Partes Review of U.S. Pat. No. 8,863,752—IPR2015-01604, Exhibit 1016, WO 00/28843 A1 to Pienemann, Jul. 20, 2015.
JT International S.A., Petition for Inter Partes Review of U.S. Pat. No. 8,863,752—IPR2015-01604, Exhibit 1017, Certified English translation of WO 00/28843 A1 to Pienemann, Jul. 20, 2015.
JT International S.A., Petition for Inter Partes Review of U.S. Pat. No. 8,863,752—IPR2015-01604, Exhibit 1018, EP 0 845 220 A1 to Susa, Jul. 20, 2015.
JT International S.A., Petition for Inter Partes Review of U.S. Pat. No. 8,863,752—IPR2015-01604, Exhibit 1019, J.A. Speck, Mechanical Fastening, Joining and Assembly (1997), Jul. 20, 2015.
Logic Technology Products, Inc., Petition for Inter Partes Review of U.S. Pat. No. 8,375,957—IPR2015-00098, Oct. 21, 2014.
Logic Technology Products, Inc., Petition for Inter Partes Review of U.S. Pat. No. 8,375,957—IPR2015-00098, Exhibit 1001—U.S. Pat. No. 8,375,957, Oct. 21, 2014.
Logic Technology Products, Inc., Petition for Inter Partes Review of U.S. Pat. No. 8,375,957—IPR2015-00098, Exhibit 1002, Declaration of Gregory Buckner, Ph.D., Oct. 21, 2014.
Logic Technology Products, Inc., Petition for Inter Partes Review of U.S. Pat. No. 8,375,957—IPR2015-00098, Exhibit 1003, China Patent CN 2719043—issue date Aug. 24, 2005, Oct. 21, 2014.
Logic Technology Products, Inc., Petition for Inter Partes Review of U.S. Pat. No. 8,375,957—IPR2015-00098, Exhibit 1004, Certified English translation of CN 2719043 pursuant to 37 C.F.R. 42.63(b), Oct. 21, 2014.
Logic Technology Products, Inc., Petition for Inter Partes Review of U.S. Pat. No. 8,375,957—IPR2015-00098, Exhibit 1005, U.S. publication 2007/0267031 ("Hon '031"), which is the U.S. equivalent of CN 2719043, Oct. 21, 2014.
Logic Technology Products, Inc., Petition for Inter Partes Review of U.S. Pat. No. 8,375,957—IPR2015-00098, Exhibit 1006, CA 2562581, which is the Canadian equivalent of CN 2719043, Oct. 21, 2014.
Logic Technology Products, Inc., Petition for Inter Partes Review of U.S. Pat. No. 8,375,957—IPR2015-00098, Exhibit 1007, U.S. Pat. No. 3,200,819 ("Gilbert")—issue date Aug. 17, 1965, Oct. 21, 2014.
Logic Technology Products, Inc., Petition for Inter Partes Review of U.S. Pat. No. 8,375,957—IPR2015-00098, Exhibit 1008, U.S. Pat. No. 2,057,353 ("Whittemore")—issue date Oct. 13, 1936, Oct. 21, 2014.
Logic Technology Products, Inc., Petition for Inter Partes Review of U.S. Pat. No. 8,375,957—IPR2015-00098, Exhibit 1009, U.S. Pat. No. 5,894,841 ("Voges")—issue date Apr. 20, 1999, Oct. 21, 2014.
Logic Technology Products, Inc., Petition for Inter Partes Review of U.S. Pat. No. 8,375,957—IPR2015-00098, Exhibit 1010, U.S. Pat. App. Pub. 2008/0257367 ("Paterno")—filed Apr. 23, 2007, Oct. 21, 2014.
Logic Technology Products, Inc., Petition for Inter Partes Review of U.S. Pat. No. 8,375,957—IPR2015-00098, Exhibit 1011, EP 0533599A1 ("Connors")—publication date Mar. 24, 1993, Oct. 21, 2014.
Logic Technology Products, Inc., Petition for Inter Partes Review of U.S. Pat. No. 8,375,957—IPR2015-00098, Exhibit 1012, Non-patent publication "What is a MOSFET, what does it look like, and how does it work?" dated May 24, 2004, printed from the Internet Archive, i.e., the Wayback machine, which was archived on Mar. 5, 2010 ("TechPowerUp"), Oct. 21, 2014.
Logic Technology Products, Inc., Petition for Inter Partes Review of U.S. Pat. No. 8,375,957—IPR2015-00098, Exhibit 1013, Non-patent publication "What is a MOSFET, what does it look like, and how does it work?" dated May 24, 2004, printed from the Internet Archive, i.e.,

(56) References Cited

OTHER PUBLICATIONS the Wayback machine, which was archived on Jul. 20, 2011 ("TechPowerUp"), Oct. 21, 2014.
Logic Technology Products, Inc., Petition for Inter Partes Review of U.S. Pat. No. 8,375,957—IPR2015-00098, Exhibit 1014, PCT application No. PCT/CN2007/001576, filed on May 15, 2007, and Jan. 15, 2009 Chinese Declaration re CN Patent Application No. 200620090805 ("Hon '805"), Oct. 21, 2014.
Logic Technology Products, Inc., Petition for Inter Partes Review of U.S. Pat. No. 8,375,957—IPR2015-00098, Exhibit 1015, '957 patent file history, Oct. 29, 2008 Preliminary Amendment, Oct. 21, 2014.
Logic Technology Products, Inc., Petition for Inter Partes Review of U.S. Pat. No. 8,375,957—IPR2015-00098, Exhibit 1016, '957 patent file history, Oct. 5, 2010, Office Action, Oct. 21, 2014.
Logic Technology Products, Inc., Petition for Inter Partes Review of U.S. Pat. No. 8,375,957—IPR2015-00098, Exhibit 1017, '957 patent file history, Mar. 7, 2011, Response to Office Action, Oct. 21, 2014.
Logic Technology Products, Inc., Petition for Inter Partes Review of U.S. Pat. No. 8,375,957—IPR2015-00098, Exhibit 1018, '957 patent file history, Mar. 29, 2011, Applicant's "Marked-Up Specification", Oct. 21, 2014.
Logic Technology Products, Inc., Petition for Inter Partes Review of U.S. Pat. No. 8,375,957—IPR2015-00098, Exhibit 1019, '957 patent file history, Jun. 8, 2011, Office Action, Oct. 21, 2014.
Logic Technology Products, Inc., Petition for Inter Partes Review of U.S. Pat. No. 8,375,957—IPR2015-00098, Exhibit 1020, '957 patent file history, Dec. 8, 2011, Request for Continued Examination, Oct. 21, 2014.
Logic Technology Products, Inc., Petition for Inter Partes Review of U.S. Pat. No. 8,375,957—IPR2015-00098, Exhibit 1021, '957 patent file history, Jan. 9, 2012, Office Action, Oct. 21, 2014.
Logic Technology Products, Inc., Petition for Inter Partes Review of U.S. Pat. No. 8,375,957—IPR2015-00098, Exhibit 1022, '957 patent file history, May 9, 2012, Amendment, Oct. 21, 2014.
Logic Technology Products, Inc., Petition for Inter Partes Review of U.S. Pat. No. 8,375,957—IPR2015-00098, Exhibit 1023, '957 patent file history, Aug. 7, 2012, Office Action, Oct. 21, 2014.
Logic Technology Products, Inc., Petition for Inter Partes Review of U.S. Pat. No. 8,375,957—IPR2015-00098, Exhibit 1024, '957 patent file history, Aug. 29, 2012, Amendment, Oct. 21, 2014.
Logic Technology Products, Inc., Petition for Inter Partes Review of U.S. Pat. No. 8,375,957—IPR2015-00098, Exhibit 1025, '957 patent file history, Dec. 17, 2012, Notice of Allowance., Oct. 21, 2014.
Logic Technology Products, Inc., Petition for Inter Partes Review of U.S. Pat. No. 8,375,957—IPR2015-00098, Exhibit 1026, '957 patent file history, Jul. 2, 2013, Certificate of Correction, Oct. 21, 2014.
Logic Technology Products, Inc., Petition for Inter Partes Review of U.S. Pat. No. 8,375,957—IPR2015-00098, Exhibit 1027, U.S. Pat. No. 8,156,944 (Hon; Aerosol Electronic Cigarette), Oct. 21, 2014.
Logic Technology Products, Inc., Petition for Inter Partes Review of U.S. Pat. No. 8,375,957—IPR2015-00098, Exhibit 1028, Decision—Institution of Inter Partes Review in IPR2013-00387, Paper 7, Oct. 21, 2014.
Logic Technology Products, Inc., Petition for Inter Partes Review of U.S. Pat. No. 8,375,957—IPR2015-00098, Exhibit 1029, Curriculum Vitae of Gregory Buckner, Ph.D., Oct. 21, 2014.
NJOY, Inc. et al, Petition for Inter Partes Review of U.S. Pat. No. 8,863,752—IPR2015-01301, May 29, 2015.
NJOY, Inc. et al, Petition for Inter Partes Review of U.S. Pat. No. 8,863,752—IPR2015-01301, Exhibit 1001, U.S. Pat. No. 8,863,752 ("the '752 patent"), May 29, 2015.
NJOY, Inc. et al, Petition for Inter Partes Review of U.S. Pat. No. 8,863,752—IPR2015-01301, Exhibit 1002, Declaration Samir Nayfeh, Ph.D. ("Nayfeh Decl."), May 29, 2015.
NJOY, Inc. et al, Petition for Inter Partes Review of U.S. Pat. No. 8,863,752—IPR2015-01301, Exhibit 1003, Canadian Pat. App. No. 2,752,134 ("Hon '134"), May 29, 2015.
NJOY, Inc. et al, Petition for Inter Partes Review of U.S. Pat. No. 8,863,752—IPR2015-01301, Exhibit 1004, U.S. Pat. No. 3,200,819 ("Gilbert"), May 29, 2015.
NJOY, Inc. et al, Petition for Inter Partes Review of U.S. Pat. No. 8,863,752—IPR2015-01301, Exhibit 1005, U.S. Pat. No. 6,155,268 ("Takeuchi"), May 29, 2015.
NJOY, Inc. et al, Petition for Inter Partes Review of U.S. Pat. No. 8,863,752—IPR2015-01301, Exhibit 1006, U.S. Pat. No. 1,446,087 ("Griffin"), May 29, 2015.
NJOY, Inc. et al, Petition for Inter Partes Review of U.S. Pat. No. 8,863,752—IPR2015-01301, Exhibit 1007, Markman Hearing/Claim Construction Order, *Fontem Ventures, B.V. v. NJOY, Inc.*, No. 14-cv-1645, Dkt. 133 (C.D. Cal. May 7, 2015), May 29, 2015.
NJOY, Inc. et al, Petition for Inter Partes Review of U.S. Pat. No. 8,863,752—IPR2015-01301, Exhibit 1008, Rulings on Claim Construction, *Fontem Ventures, B.V. v. NJOY, Inc.*, No. 14-cv-1645, Dkt. 65 (C.D. Cal. Jan. 29, 2015), May 29, 2015.
NJOY, Inc. et al, Petition for Inter Partes Review of U.S. Pat. No. 8,863,752—IPR2015-01301, Exhibit 1009, Joint Claim Construction and Prehearing Statement, *Fontem Ventures, B.V. v. NJOY, Inc.*, No. 14-cv-1645, Dkt. 93 (C.D. Cal. Mar. 19, 2015), May 29, 2015.
NJOY, Inc. et al, Petition for Inter Partes Review of U.S. Pat. No. 8,863,752—IPR2015-01301, Exhibit 1010, Revised Joint Claim Construction and Prehearing Statement, *Fontem Ventures, B.V. v. NJOY, Inc.*, No. 14-cv-1645, Dkt. 34 (C.D. Cal. Sep. 30, 2014), May 29, 2015.
NJOY, Inc. et al, Petition for Inter Partes Review of U.S. Pat. No. 8,863,752—IPR2015-01301, Exhibit 1011, Curriculum Vitae of Samir Nayfeh, Ph.D., May 29, 2015.
NJOY et al., Defendants' Joint Invalidity Contentions, Case No. CV-14-01645 etc., Aug. 7, 2014.
NJOY, Inc. et al., Defendants' Joint Invalidity Contentions, CV-14-01645 etc., Attachment D—Claim Charts for U.S. Pat. No. 8,375,957, Aug. 7, 2014.
NJOY, Inc. et al., Defendants' Joint Invalidity Contentions, Case No. CV-14-01645 etc., Feb. 26, 2015.
NJOY, Inc. et al., Defendant's Joint Invalidity Contentions, CV14-01645 etc., Exhibit D—Claim Charts for U.S. Pat. No. 8,863,752, Feb. 26, 2015.
State Intellectual Property Office China PRC, Decision of Patent Invalidation Petition for CNZL200620090805.0, Mar. 3, 2014.
State Intellectual Property Office China PRC, Examination Decision on the Invalidity Declaration Application for CNZL200620090805.0, Jun. 23, 2010.
State Intellectual Property Office PRC China, English translation of Written Opinion for PCT/CN07/001576, Aug. 16, 2007.
State Intellectual Property Office PRC China, International Search Report for PCT/CN07/001576, Aug. 16, 2007.
State Intellectual Property Office PRC China, Search Report for Utility Model CNZL200620090805.0, Nov. 18, 2008.
TechPowerUp Internet Webpage, http://www.techpowerup.com/articles/overclocking/voltmods/21, May 24, 2004.
USPTO, Final Office Action for U.S. Appl. No. 12/226,819, Jun. 8, 2011.
USPTO, Non-Final Office Action for U.S. Appl. No. 12/226,819, Aug. 7, 2012.
USPTO, Non-Final Office Action for U.S. Appl. No. 12/226,819, Jan. 9, 2012.
USPTO, Non-Final Office Action for U.S. Appl. No. 12/226,819, Oct. 5, 2010.
USPTO, Non-Final Office Action for U.S. Appl. No. 13/915,427, Mar. 21, 2014.
USPTO, Non-Final Office Action for U.S. Appl. No. 13/754,521, Sep. 25, 2015.
USPTO, Notice of Allowance for U.S. Appl. No. 12/226,819, Dec. 17, 2012.
USPTO, Notice of Allowance for U.S. Appl. No. 13/915,427, Aug. 19, 2014.

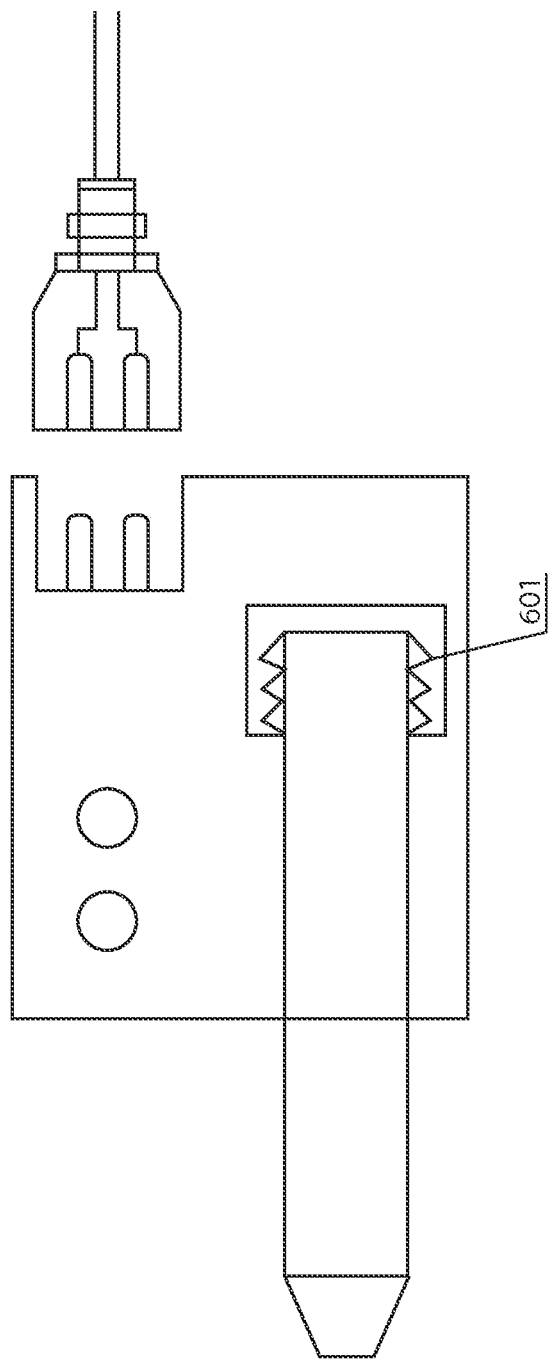

ELECTRONIC CIGARETTE

CROSS-REFERENCE TO RELATED APPLICATIONS

This application is a continuation of U.S. patent application Ser. No. 13/754,521, filed Jan. 30, 2013, and now pending, which is a continuation of U.S. patent application Ser. No. 12/226,819, filed Jan. 15, 2009, and now U.S. Pat. No. 8,375,957, which is a 371 national phase application of International Patent Application No. PCT/CN2007/001576, filed May 15, 2007 and now converted, which claims the benefit of Chinese Patent Application No. 200620090805.0, filed May 16, 2006. All of these applications are incorporated herein by reference in their entirety.

BACKGROUND

Although smoking causes serious respiratory diseases and cancers, it is difficult to get smokers to quit smoking. Nicotine is the effective ingredient in cigarettes. Nicotine is a micromolecular alkaloid which is basically harmless to humans at low dosages. Tar is the major harmful substance in tobacco. Tobacco tar contains thousands of ingredients, dozens of which are carcinogenic.

Cigarette substitutes have used relatively pure nicotine in patches, chewing gum and aerosols. Still disadvantages remain with cigarette substitutes or products for helping smokers to quit smoking.

SUMMARY OF THE INVENTION

An improved electronic cigarette has a battery assembly, an atomizer assembly and a cigarette bottle assembly. The battery assembly connects with one end of the atomizer assembly, and the cigarette bottle assembly is inserted into the other end of the atomizer assembly, thus forming one cigarette type or cigar type body. Use of the electronic cigarette reduces cancer risks and fire hazards while providing a simulated smoking experience.

BRIEF DESCRIPTION OF THE DRAWINGS

FIG. 6 is a diagram of a charger.

DETAILED DESCRIPTION OF THE DRAWINGS

Figure 1:
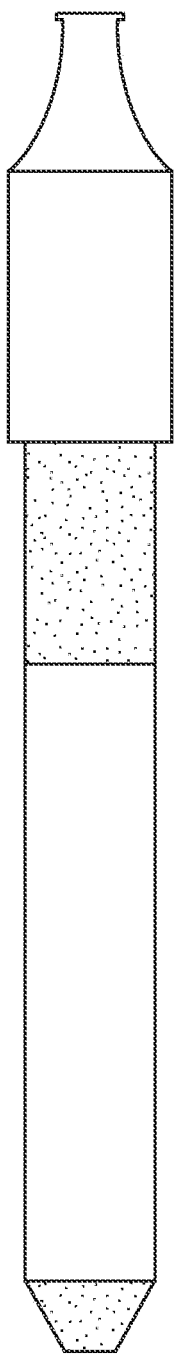
FIG. 1 is a side view of an electronic cigarette.
Figure 2A:
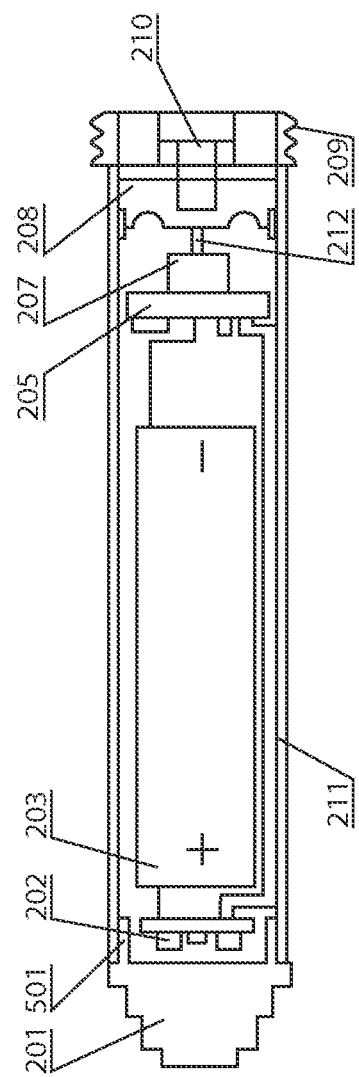
FIG. 2A is a view of the battery assembly.

As shown in FIG. 1, an electronic cigarette has an appearance similar to a cigarette inserted into the cigarette holder. As shown in FIG. 2A, the electronic cigarette includes a battery assembly, an atomizer assembly and a cigarette bottle assembly. An external thread electrode (209) is located in one end of the battery assembly, and an internal thread electrode (302) is located in one end of the atomizer assembly. The battery assembly and atomizer assembly are connected through the screw thread electrode into an electronic cigarette. The cigarette bottle assembly is inserted into the other end of atomizer assembly.

As shown in FIG. 2A, the battery assembly includes an indicator (202), lithium ion battery (203), MOSFET electric circuit board (205), sensor (207), silica gel corrugated membrane (208), primary screw thread electrode (209), primary negative pressure cavity (210), and primary shell (211). On one end of the primary shell (211) is an external thread electrode (209). On the other end is an indicator (202), where there is an indicator cap (201) on one side having a small hole (501). On the other side, the lithium ion battery (203) and MOSFET (Metallic Oxide Semiconductor Field Effect Tube) electric circuit board (205) are connected successively. The sensor (207) is located on MOSFET electric circuit board (205). Between the primary screw thread electrode (209) and sensor (207) is a silica gel corrugated membrane (208), on which there is the primary negative pressure cavity (210). The sensor (207) is connected with the silica gel corrugated membrane (208) through the switch spring (212).

The sensor (207) may be switch sensor made of elastic alloy slice, a linear output Hall sensor, a semiconductor force-sensitive chip, a semiconductor matrix thermoelectric bridge chip, capacitance or inductance sensor. The indicators (202) include two red LEDs. The lithium ion battery (203) may be either a rechargeable polymer lithium ion battery or a rechargeable lithium ion battery. The external thread electrode (209) is a gold-coated stainless steel or brass part with a hole drilled in the center. The silica gel corrugated membrane (208) may alternatively be made of fluorinated rubber, butyronitrile rubber, or elastic alloy film.

Figure 3:
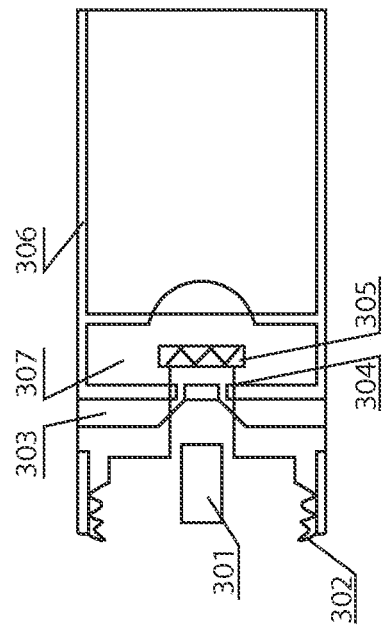
FIG. 3 is the diagram of the atomizer assembly.

As shown in FIG. 3, the atomizer assembly includes the internal thread electrode (302), air-liquid separator (303), atomizer (307) and the secondary shell (306). One end of the secondary shell (306) is inserted into the cigarette bottle assembly for connection, while the other end has an internal thread electrode (302), in which there is the secondary negative pressure cavity (301). The air-liquid separator (303) and the atomizer (307) are connected with the internal thread electrode (302) successively. On the secondary shell (306), there is an air intake hole (502). The air-liquid separator (303) is made of stainless steel or plastic with a hole. The internal thread electrode (302) is a gold-coated stainless steel or brass part with a hole in the center.

Figure 4:
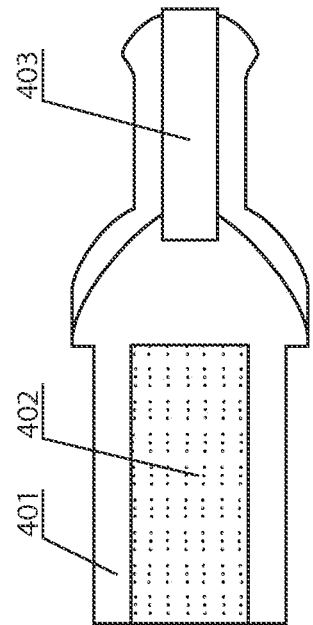
FIG. 4 is the diagram of the cigarette bottle assembly.
Figure 8:
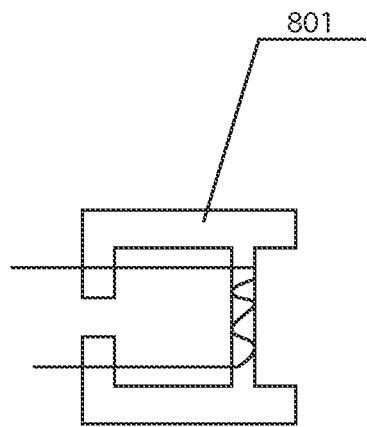
FIG. 8 is a side view of an atomizer.
Figure 9:
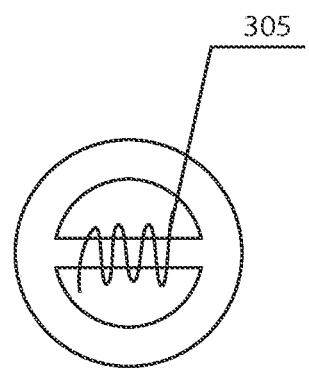
FIG. 9 is an end view of the atomizer shown in FIG. 8.
Figure 10:
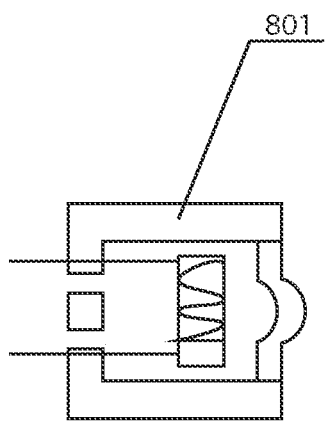
FIG. 10 is a diagram of a spray atomizer.
Figure 11:
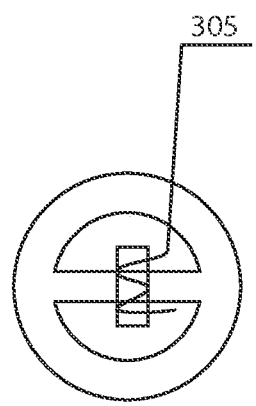
FIG. 11 is an end view of the atomizer shown in FIG. 10.

The atomizer (307) may be a capillary impregnation atomizer as in FIGS. 8 and 9, or a spray atomizer as in FIGS. 10 and 11. As shown in FIG. 4, the cigarette bottle assembly includes the cigarette liquid bottle (401), fiber (402) and suction nozzle (403). The fiber (402) containing cigarette liquid is located on one end of the cigarette liquid bottle (401). This end is inserted into the secondary shell (306) and lies against the atomizer (307). The suction nozzle (403) is located on the other end of the cigarette liquid bottle (401). Between the fiber (402) and interior wall of the cigarette liquid bottle (401) is an air intake hole (503).

Figure 5A:
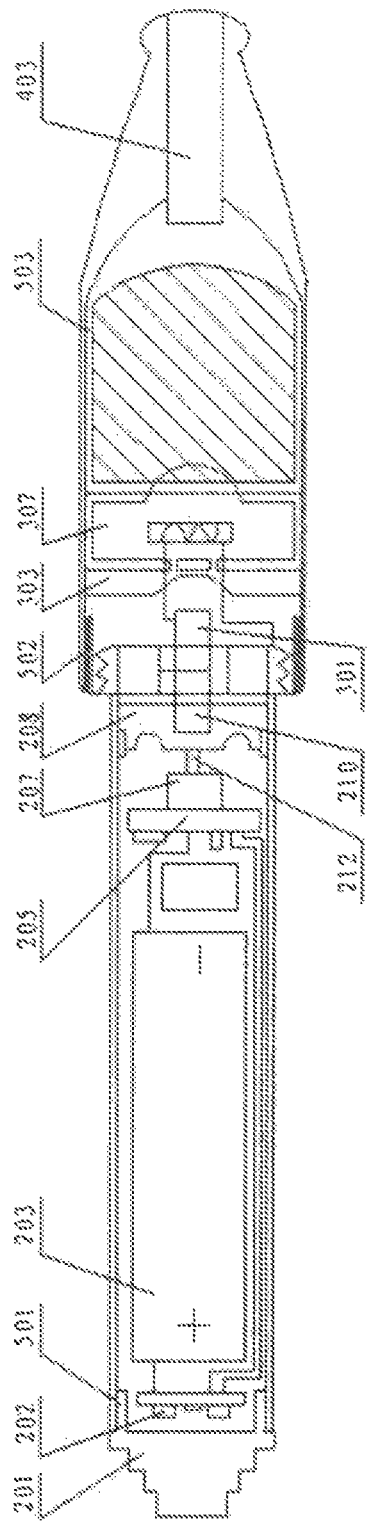
FIG. 5A is a section view of an electronic cigarette.

As shown in FIG. 5A, the standby state has the fully charged battery assembly shown on FIG. 2A fastened onto the atomizer assembly shown on FIG. 3, which is then inserted into the cigarette bottle assembly shown in FIG. 4. When the user slightly sucks the suction nozzle (403), negative pressure forms on the silica gel corrugated membrane (208) through the air intake hole (503) and the primary and secondary negative pressure cavities (210, 301). The silica gel corrugated membrane (208), under the action of suction pressure difference, distorts to drive the switch spring (212) and sensor (207), thus switching MOSFET electric circuit board (205).

At this moment, the indicators (202) are lit gradually; the lithium ion battery (203) electrifies the heating body (305) inside the atomizer (307) through MOSFET electric circuit board (205) as well as the internal and external thread electrodes (302, 209).

The heating body (305) inside the atomizer (307) produces heat. The fiber (402) inside the cigarette liquid bottle (401) contains cigarette liquid, which soaks the micro-porous ceramics (801) inside the atomizer through the fiber (402). The air enters through the air intake hole (502), passes through the run-through hole on the air-liquid separator (303), and helps to form air-liquid mixture in the spray nozzle (304) of the atomizer (307). The air-liquid mixture sprays onto the heating body (305), gets vaporized, and is quickly absorbed into the airflow and condensed into aerosol, which passes through the air intake hole (503) and suction nozzle (403) to form white mist type aerosol.

When suction stops, the switch spring (212) and sensor (207) are reset; the atomizer (307) stops working; the indicators (202) gradually die down. When the operation times reaches the pre-set value, the atomizer (307) provides a work delay of 5-20 seconds per time, so as to remove the micro-dirt accumulated on the heating body (305).

Besides the micro-porous ceramics, the liquid supply material of the atomizer (307) may also be foamed ceramics, micro-porous glass, foamed metal, stainless steel fiber felt, terylene fiber, nylon fiber, nitrile fiber, aramid fiber or hard porous plastics. The heating body (305) is made of the micro-porous ceramics on which nickel-chromium alloy wire, iron-chromium alloy wire, platinum wire, or other electro thermal materials are wound. Alternatively, it may be a porous component directly made of electrically conductive ceramics or PTC (Positive Temperature Coefficient) ceramics and associated with a sintered electrode. The surface of the heating body (305) is sintered into high-temperature glaze to fix the zeolite grains, which are made of natural zeolite, artificial non-organic micro-porous ceramics or aluminum oxide grains. The cigarette liquid bottle (401) and suction nozzle (403) in the cigarette bottle assembly are made of non-toxic plastic. The fiber (402) inside of them is made of polypropylene fiber or nylon fiber to absorb cigarette liquid. In the battery assembly, there is a fine hole (501) on the indicator cap (201) for balancing the pressure difference on both sides of the silica gel corrugated membrane (208).

The cigarette liquid contains 0.1-3.5% nicotine, 0.05-5% tobacco flavor, 0.1-3% organic acid, 0.1-0.5% stabilizer, and propanediol for the remaining.

The primary and secondary shells (211, 306) are made of stainless steel tube or copper alloy tube with baked-enamel coating of real cigarette color.

Figure 12:
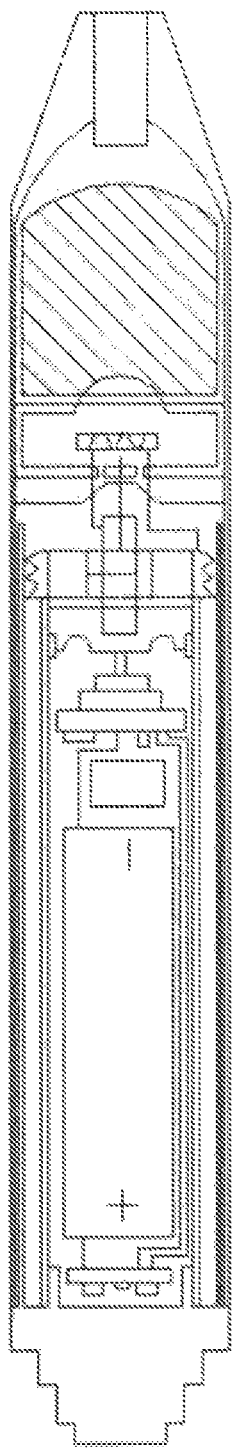
FIG. 12 is a section view of another embodiment.

As shown in FIG. 12, the diameter of the battery assembly may be increased in proportion, so that it is consistent with the diameter of the atomizer assembly. Its shell may be decorated with the leaf veins and sub-gloss brown-yellow baked-enamel coating, to create a cigar type device.

For charging the lithium ion battery (203), the screw thread electrode (601) matches the external thread electrode (209) on the battery assembly, so that it may be used as the charging interface.

Figure 2B:
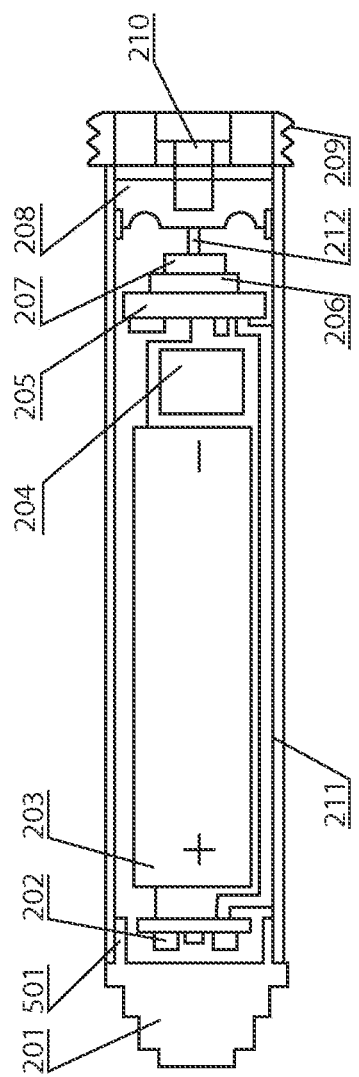
FIG. 2B is a view of another battery assembly.

The design in FIG. 2B is difference from the design in FIG. 1A as follows: Microcircuit (206) is added between MOSFET electric circuit board (205) and sensor (207). On the surface of the primary shell (211), there is a screen (204) for display of the power of the lithium ion battery (203) and the sucking times.

Figure 5B:
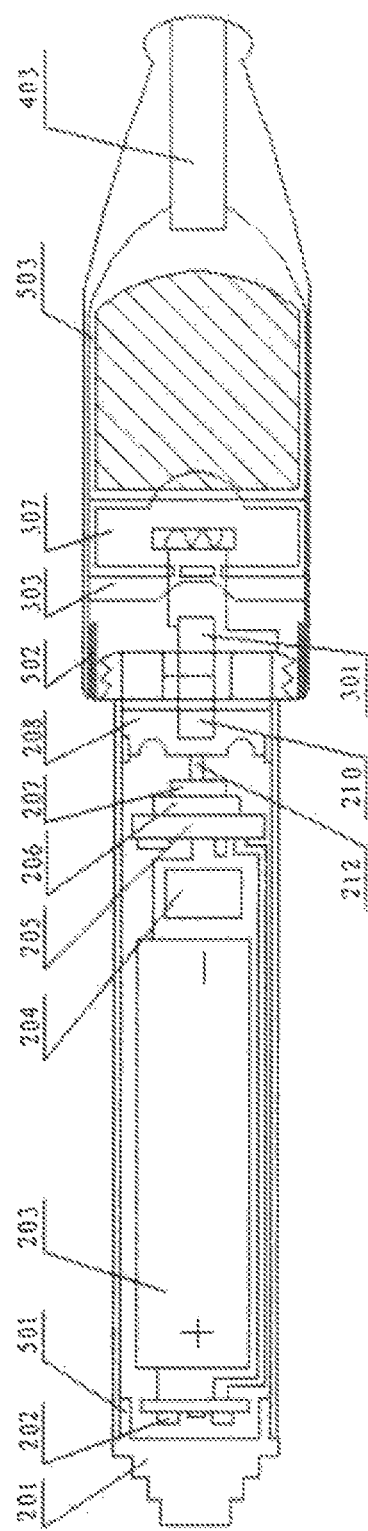
FIG. 5B is a section view of another embodiment.

As shown in FIG. 5B, a fully charged battery assembly is attached onto the atomizer assembly, which is then inserted into the cigarette bottle assembly shown on FIG. 4. When the user slightly sucks the suction nozzle (403), negative pressure forms on the silica gel corrugated membrane (208) through the air intake hole (503) and the primary and secondary negative pressure cavities (210, 301). The silica gel corrugated membrane (208), under the action of suction pressure difference, distorts to drive the switch spring (212) and sensor (207), thus activating the Microcircuit (206) and MOSFET electric circuit board (205). At this moment, the indicators (202) are lit gradually; the lithium ion battery (203) electrifies the heating body (305) inside the atomizer (307) through MOSFET electric circuit board (205) as well as the internal and external thread electrodes (302, 209), so that the heating body (305) inside the atomizer (307) produces heat.

The fiber (402) inside the cigarette liquid bottle (401) contains cigarette liquid, which soaks the micro-porous ceramics (801) inside the atomizer through the fiber (402). The air enters through the air intake hole (502), passes through the run-through hole on the air-liquid separator (303), and helps to form air-liquid mixture in the spray nozzle (304) of the atomizer (307). The air-liquid mixture sprays onto the heating body (305), gets vaporized, and is quickly absorbed into the airflow and condensed into aerosol, which passes through the air intake hole (503) and suction nozzle (403) to form white mist type aerosol.

Figure 7:
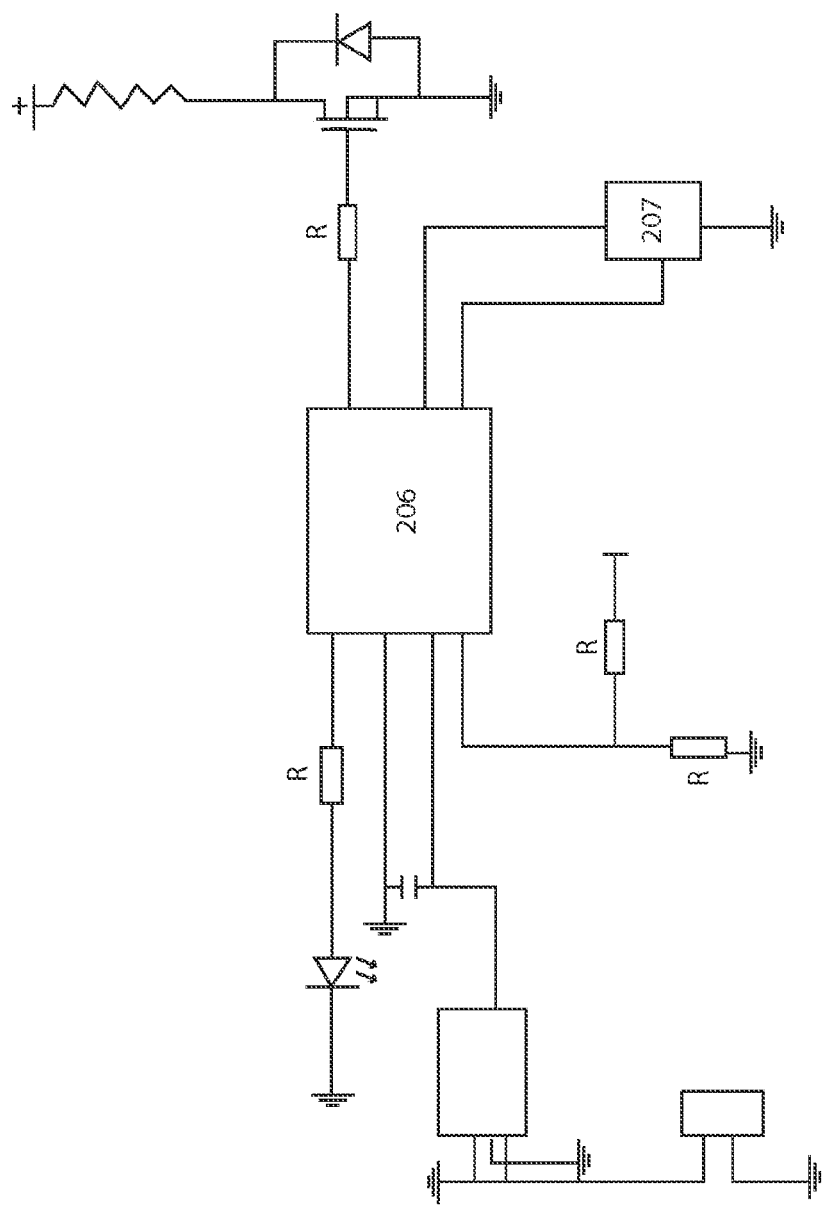
FIG. 7 is the electric circuit diagram.

As shown in FIG. 7, when the action of suction activates the sensor, Microcircuit (206) scans the sensor (207) in the power-saving mode of pulse, and according to the signal parameters of the sensor (207), restricts the atomizing capacity with the integral function of frequency to single operation time. Also, the microcircuit (206) accomplishes the pulse width modulation and over discharging protection for the constant power output, automatic cleansing for thousands of times per operation, step lighting/dying down control of the indicator, display of the operation times and battery capacity, automatic recovery after sensor malfunction shutdown, etc.

The unit and its connecting structure may also be loaded with drugs for delivery to the lung.

Above are just specifications of an example and do not necessarily restrict the scope of protection. Any equivalent modification made on the basis of the design spirit shall fall into the scope of protection.

The invention claimed is:

1. An atomizer assembly used with a battery assembly to provide an electronic cigarette comprising:
    a tubular atomizer assembly housing having a first end and a second end;
    an atomizer and a liquid supply in the tubular atomizer assembly housing;
    an inner electrode and an outer electrode at the first end of the tubular atomizer assembly housing, with the inner electrode concentric with the outer electrode;
    with the atomizer including a heater wire wound on a porous body and the porous body perpendicular to a central longitudinal axis of the tubular atomizer assembly housing, with the heater wire having a first lead connected to the inner electrode and a second lead connected to the outer electrode; and
    an airflow path through the tubular atomizer assembly housing from the atomizer to an outlet at the second end of the tubular atomizer assembly housing.

2. The atomizer assembly of claim 1 further including a through hole centered on the central longitudinal axis of the tubular atomizer assembly housing, and with the through hole leading to the airflow path.

3. The atomizer assembly of claim 2 with the through hole at a center of the inner electrode.

4. The atomizer assembly of claim 3 with the porous body comprising a fiber material.

5. The atomizer assembly of claim 4 further including a liquid supply in the tubular atomizer assembly housing in contact with the porous body.

6. The atomizer assembly of claim 5 with the liquid supply containing a liquid including 0.1-3.5% nicotine.

7. The atomizer assembly of claim 5 with the fiber material confined within inner cylindrical walls of the tubular atomizer assembly housing.

8. The atomizer assembly of claim 7 further including an air passageway within the tubular atomizer assembly housing around the liquid supply.

9. The atomizer assembly of claim 4 further including a mouthpiece at the second end of the tubular atomizer assembly housing, and with the outlet in the mouthpiece.

10. The atomizer assembly of claim 9 wherein the mouthpiece is removable from the second end of the tubular atomizer assembly housing.

11. An atomizer assembly component of an electronic cigarette comprising:
   a tubular atomizer assembly housing having a first end and a second end;
   an atomizer and a liquid supply in the tubular atomizer assembly housing;
   an inner electrode and an outer electrode at the first end of the tubular atomizer assembly housing, with the inner electrode concentric with the outer electrode;
   with the atomizer including a heater wire wound on a porous body comprising a fiber material, and the porous body perpendicular to a central longitudinal axis of the tubular atomizer assembly housing, with the heater wire having a first lead connected to the inner electrode and a second lead connected to the outer electrode;
   an airflow path through the tubular atomizer assembly housing from the atomizer to an outlet at the second end of the tubular atomizer assembly housing;
   a through hole at a center of the inner electrode leading into the airflow path;
   a liquid supply in the tubular atomizer assembly housing in contact with the porous body, with the liquid supply containing a liquid including nicotine.

12. The atomizer assembly of claim 11 further including an air passageway within the tubular atomizer assembly housing around the liquid supply.

13. The atomizer assembly of claim 12 further including a mouthpiece at the second end of the tubular atomizer assembly housing, and with the outlet in the mouthpiece.

14. The atomizer assembly of claim 13 wherein the mouthpiece is removable from the second end of the tubular atomizer assembly housing.

15. An atomizer assembly component of an electronic cigarette comprising:
   a tubular atomizer assembly housing having a first end and a second end;
   a mouthpiece having an outlet at the second end of the tubular atomizer assembly housing;
   an atomizer and a liquid supply in the tubular atomizer assembly housing;
   an inner electrode and an outer electrode at the first end of the tubular atomizer assembly housing, with the inner electrode concentric with the outer electrode;
   with the atomizer including a heater wire wound on a porous body comprising a fiber material, and the porous body perpendicular to a central longitudinal axis of the tubular atomizer assembly housing, with the heater wire having a first lead connected to the inner electrode and a second lead connected to the outer electrode;
   an airflow path through the tubular atomizer assembly housing from the atomizer to an outlet at the second end of the tubular atomizer assembly housing;
   a through hole at a center of the inner electrode leading into the airflow path;
   a liquid supply in the tubular atomizer assembly housing in contact with the porous body, with the liquid supply containing a liquid including nicotine.

* * * * *